United States Patent
Huang et al.

(10) Patent No.: US 6,642,150 B1
(45) Date of Patent: Nov. 4, 2003

(54) METHOD FOR TESTING FOR BLIND HOLE FORMED IN WAFER LAYER

(75) Inventors: Chuan-Chieh Huang, Hsin-Chu (TW);
Wen-Hsiang Tang, Hsin-Chu (TW);
Ming-Shuo Yen, Hsin-Chu (TW);
Chiang-Jen Peng, Hsin-Chu (TW);
Pei-Hung Chen, Hsin-Chu (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 0 days.

(21) Appl. No.: 09/473,029

(22) Filed: Dec. 28, 1999

(51) Int. Cl.[7] .............................................. H01L 21/302
(52) U.S. Cl. .............................. 438/714; 438/7; 438/8; 438/9; 438/14; 438/16; 216/59; 216/60
(58) Field of Search .................... 438/7, 8, 9, 16, 438/14, 719; 216/59, 60, 79

(56) References Cited

U.S. PATENT DOCUMENTS

| | | | |
|---|---|---|---|
| 4,717,446 A | 1/1988 | Nagy et al. | 156/626 |
| 4,797,939 A | 1/1989 | Hoki et al. | 382/8 |
| 5,465,154 A | 11/1995 | Levy | 356/382 |
| 5,465,859 A | 11/1995 | Chapple-Sokol et al. | 216/12 |
| 5,493,116 A | 2/1996 | Toro-Lira et al. | 250/310 |
| 5,637,186 A | 6/1997 | Liu et al. | 438/14 |
| 5,694,207 A | 12/1997 | Hung et al. | 356/72 |
| 6,091,488 A | * 7/2000 | Bishop | 356/237.5 |
| 6,121,156 A | 9/2000 | Shamble et al. | 438/734 |
| 6,162,735 A | 12/2000 | Zimmermann et al. | 438/712 |

FOREIGN PATENT DOCUMENTS

| | | | |
|---|---|---|---|
| JP | 01-109717 | * | 4/1989 |
| JP | 09-232400 | * | 9/1997 |
| JP | 10-321130 | * | 12/1998 |
| JP | 10-332535 | * | 12/1998 |
| JP | 11-260802 | * | 9/1999 |

* cited by examiner

Primary Examiner—George Goudreau
(74) Attorney, Agent, or Firm—George O. Saile; Stephen B. Ackerman; William Robertson

(57) ABSTRACT

A new method for detecting blind holes in the contact layer of a multi-chip semiconductor test wafer makes use of the fact that if the hole is not a blind hole, a subsequent etch step extends the hole a predetermined distance into the layer immediately underlying the contact layer. After a predetermined number of holes have been etched through the contact layer and for a predetermined distance into the layer underlying the contact layer, the contact layer is stripped to expose the holes in the underlying layer. These holes are scanned optically by a commercial apparatus that ordinarily detects wafer defects that resemble the holes. The missing holes are detected by comparing the holes of different chips on the test wafer. The test is particularly useful with a high density plasma etch because these holes typically have a very small diameter in relation to the thickness of the contact layer.

1 Claim, 2 Drawing Sheets

METHOD FOR TESTING FOR BLIND HOLE FORMED IN WAFER LAYER

FIELD OF THE INVENTION

This invention relates generally to the manufacture of circuit devices on semiconductor wafers and more specifically to a method for testing an etch process for its likelihood of producing a manufacturing defect called a blind hole that can occur in a contact layer of a wafer.

INTRODUCTION

The circuit device chips of a semiconductor wafer are commonly formed as a multilayer structure. Some layers, called contact layers, form electrical interconnections between circuit nodes in the structures above and below the contact layer. A wafer can have several contact layers, and the layer below the contact layer can be the substrate or one of the layers that are formed over the substrate.

The contact layer is formed initially as a layer of dielectric material. The dielectric is commonly silicon dioxide (called oxide). An interconnection is in the form of a cylinder of metal or other conductive material that extends through the dielectric from the layer above to the layer or substrate below. The dielectric supports the conductors, and it initially acts as a template for forming the interconnections. Commonly, the interconnections are formed by first creating cylindrical holes at selected positions in the contact layer.

When the contact layer is located over the substrate, a hole in the dielectric layer extends into the substrate for a distance that is suitable for making electrical contact to circuit nodes at this location in the substrate. The hole through the dielectric of the contact layer and the substrate hole are then filled with any suitable conductor, commonly tungsten.

The holes in the contact layer can be formed in any suitable way, but this invention is particularly intended for use with a high density plasma etch. Because the holes are long in relation to their diameter, etching can sometimes form only a partial hole: a hole that does not extend completely through the dielectric of the contact layer. The resulting partial hole is called a blind hole. When a conductor is formed in a blind hole; it does not make electrical contact with the circuit node in the substrate below the contact layer.

Wafers commonly have several contact layers and the problem of blind holes can occur in any layer.

THE PRIOR ART

The holes can be detected at the surface of the contact layer but blind holes can not be distinguished from normal holes in this way.

Blind hole defects can be detected by sectioning the wafer through one or more holes and then viewing the section with a scanning electron microscope. A normal hole and a blind hole can be clearly distinguished in this test, but the test is time consuming and only a few holes can be tested.

SUMMARY OF THE INVENTION

One object of our invention is to provide a new and improved method for detecting blind holes. A more specific object is to provide a new and improved method for processing a test wafer to determine how the associated etch process affects the number of blind holes in the contact layer.

After the holes are etched in the dielectric of the contact layer in a first etch step and in the underlying layer in a second etch step, we strip the contact layer to expose the underlying surface. It is an advantage of our test method that these two etch steps are used in the same way in wafer manufacture.

A wafer has a repeating pattern of identical units which are called chips. The number of holes in a contact layer depends on the chip design, but a chip may have more than ten thousand holes. A problem occurring on contact etchers or in the etching process can induce a blind contact, and the blind contact might occur randomly on any contact hole. The location of these blind holes can not be predicted beforehand.

Therefore, we use a known optical apparatus to provide a view of the wafer, and we compare the contact pattern between each chip to find out if any blind hole has occurred. The data from this comparison is a useful indicator of the effectiveness of the process for etching the contact layer.

Other objects and features of our invention will appear in the description of the preferred embodiment of the invention.

THE DRAWING

THE PREFERRED EMBODIMENT

Introduction—A Memory Chip

It will be helpful to describe features of a dynamic memory chip that illustrate the problem of blind holes. A memory chip has a substrate with FETs that form an array of storage elements, and it three contact layers formed over the substrate. Word lines, bit lines and other conductors and circuit nodes are located on the substrate and at the interfaces of the contact layers. Holes for contacts extend through various combinations of the contact layers.

Where a conductor at one interface is connected both upward and downward to conductors or circuit nodes above and below, separate etch steps are performed for the upper and lower holes (because the lower hole is formed and filled before the overlying contact layer is formed). The conductors at opposite ends of a contact can be of different materials, for example tungsten silicide and polycrystalline silicon. These etch steps can be performed by different etch techniques.

Figure 1A:
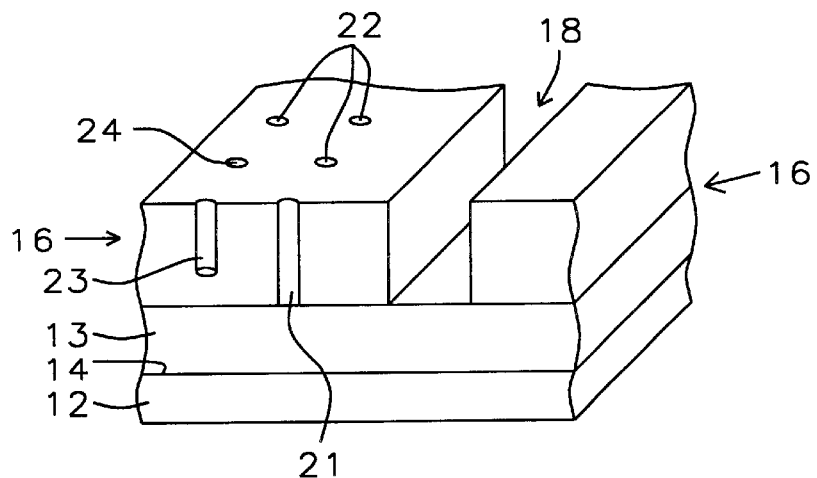
FIGS. 1A–1C are section views of a semiconductor test wafer showing successive manufacturing steps in which contact holes are formed in a dielectric interlayer and the wafer is prepared for testing for blind holes.
Figure 1B:
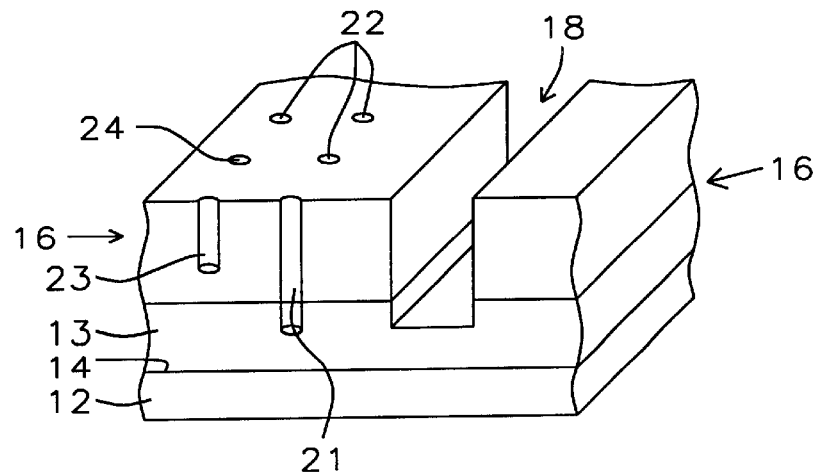
Figure 1C:
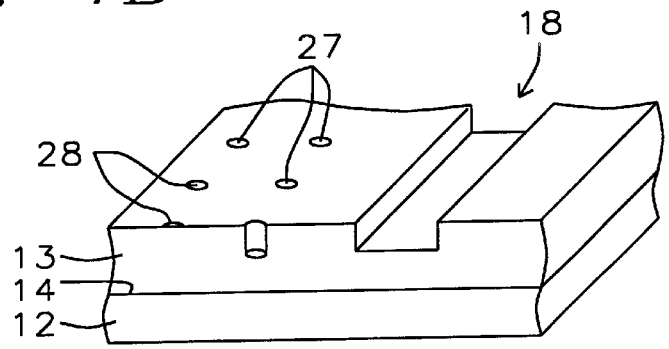

Preparing the Test Wafer—FIGS. 1A, 1B and 1C

FIG. 1A shows a silicon substrate 12, a layer 13 of polysilicon formed over the surface 14 of the substrate, and a contact layer 16. Polysilicon is a conductor and layer 13 is formed into a pattern of conductors interconnecting various circuit nodes, for example the contacts of contact layer 16. The relation of this structure to the memory chip described above will be understood without specific explanation. The dielectric of layer 16 is preferably silicon dioxide (oxide).

As has been explained already, sectioning the wafer in the way represented in FIGS. 1A, 1B, and 1C has been done in the prior art for detecting blind holes. However, our invention avoids this sectioning and the sections are shown in the drawing only to illustrate the wafer structure.

In a conventional process step, a channel 18 for a scribble line (FIGS. 1B and 1C) is formed in contact layer 16. The wafer is later broken along the scribble lines to separate the chips.

During the process step for forming channel 18, contact holes 21 through 24 are formed in contact layer 16. Hole 21 is a normal hole shown in section and holes 22 are normal holes shown in FIG. 1A only at the upper surface 25 of the contact layer 16. Hole 23 is a blind hole shown in section and hole 24 is a blind hole shown in FIG. 1A only at the upper surface 25 of the contact layer 16. (Conductors are formed in the holes in a later manufacturing step and are not shown in the drawing.)

In the step illustrated in FIG. 1B, the polysilicon layer 13 is selectively etched through channel 18 and holes 21 through 24 to extend these openings partly into layer 13.

This etch step is performed by polysilicon etchers, which are commonly used in wafer manufacture and which have a very high polysilicon to oxide etch selectivity. Thus, the polysilicon layer 13 below the normal holes 21, 22 can be etched through. The polysilicon layer 13 below blind holes 23 and 24 cannot be etched through because some oxide layer remains at the bottom of blind holes 23 and 24. The oxide that cannot be etched by this step can be seen in FIG. 1B below blind hole 23.

Note that the scribble line and the holes are not etched completely through layer 13 to the wafer surface 14.

Holes 21 through 24 can be etched in any suitable way, but the preferred etch is by high density plasma etching with $C_2F_6$ (primarily because the holes are deep in relation to their diameter). A chemical reaction takes place between the silicon and the fluorine and the product of the silicon and the fluorine is removable. This etch process is well known and its relation to the invention will be understood without further explanation.

We prepare the wafer for testing by stripping the contact layer 16 from the substrate as FIG. 1C represents. (Techniques for stripping the dielectric are commonly used in wafer manufacture and will be understood without a specific explanation.)

The presence of a hole 27 in polysilicon layer 13 means that a normal hole 21 has been formed in the contact layer 16. However, the absence of a substrate hole, indicated by a dashed line circle 28, means that a blind hole has been formed in the dielectric layer.

From a more general standpoint, polysilicon layer 13 is the layer directly underlying the contact layer 16, and the test that has been described so far can be performed in the same way with different materials forming the wafer surface 12 or otherwise directly underlying the contact layer.

Figure 2:
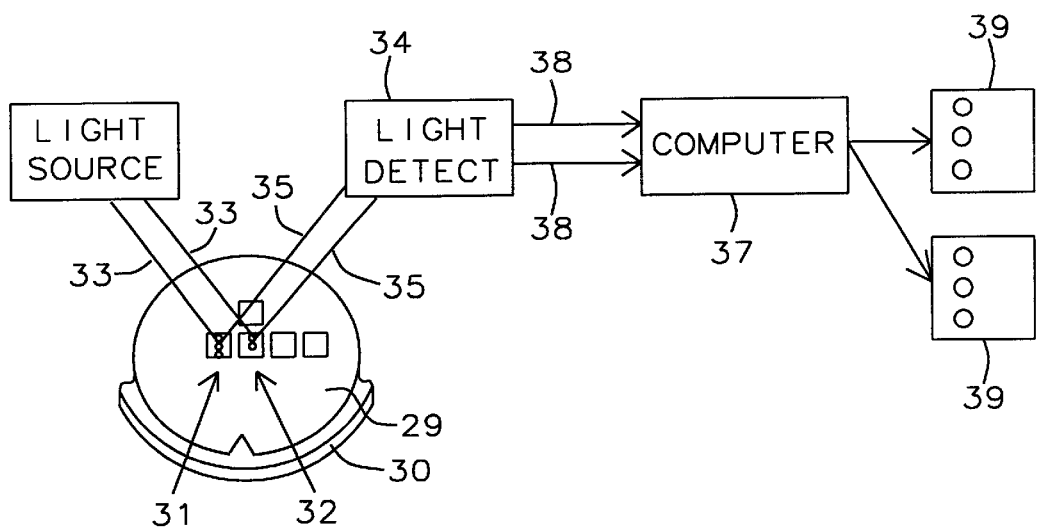
FIG. 2 is a diagram of the apparatus used in our test.

The Test Apparatus—FIG. 2

In the simplified drawing of FIG. 1C, the missing holes 28 are clearly visible and are easily counted. However, simply viewing the holes in this way is not a practical way to quantify the holes because the holes are very small and because there will often be so many holes that they are difficult to count manually.

Our test uses a commercially available apparatus manufactured by KLA. The relevant functions of this particular apparatus can be achieved by similar products or by apparatus constructed to provide these functions, and it will not be necessary to describe the features of the apparatus that are unrelated to the invention.

FIG. 2 shows the test wafer 29 carried on a support 30 of the test apparatus. The drawing shows representative chips 31 and 32. The apparatus has a light source that directs light onto the test wafer along an optical path 33 and scans all of the chips of the wafer. A light detector 34 receives reflected light from each chip along an optical path 35 and produces an output 38. A computer 37 receives detector input 38 and produces an output 39 for each chip.

This apparatus is conventionally capable of organizing the data in various ways that can be used in our method for analyzing the problem of blind holes. The computer produces a chip map with holes found in the polysilicon layer of each chip. The holes found on each chip can be compared with the holes expected on the chips, but preferably computer 37 is programmed to compare the holes found on each chip of the test wafer and to indicate when a chip is missing a hole that exists on other chips. The apparatus has conventional means for displaying the results to people making the test. As already explained, the number of blind holes is an indicator of the effectiveness of the process for etching holes 22 through 24 in the contact layer. Preferably, since a single hole makes a chip defective, the percentage of defective chips on the test wafer is be taken as the indicator of the effectiveness of the etch step.

SUMMARY

From the description of a preferred embodiment of our invention, those skilled in the art will recognize variations within the skill of the art and the intended scope of the claims.

What is claimed is:

1. A method for testing an etch process for its likelihood of producing a blind hole in a contact layer of a semiconductor wafer, comprising the following steps, providing a multi-chip test wafer, each chip having a substrate, a first layer overlying the substrate, and a contact layer overlying the first layer, etching first chips with a first etch process and etching other chips with a second etch process, etching the contact layer to produce an identical pattern of holes through the contact layer of each chip, this etching step having a likelihood of producing one or more blind holes that do not extend through the contact layer, then etching the first layer through the holes in the contact layer, each chip having the same number of holes in its first layer except for missing holes caused by blind holes in the contact layer, stripping the contact layer from the wafer to expose holes etched in the first layer, and then separately quantifying the number of blind holes in the contact layer of said first chips and said other chips by the absence of a corresponding hole in the first layer, whereby said first and second etch processes are compared for their likelihood of producing blind holes.

* * * * *